United States Patent [19]
Morton

[11] Patent Number: 6,146,350
[45] Date of Patent: Nov. 14, 2000

[54] ANKLE BRACE WITH REMOVABLE SINGLE PIECE HINGE

[75] Inventor: Scott T. Morton, New Albany, Ind.

[73] Assignee: Active Ankle Systems, Inc., Louisville, Ky.

[21] Appl. No.: 09/243,396

[22] Filed: Feb. 1, 1999

Related U.S. Application Data

[60] Provisional application No. 60/073,098, Jan. 30, 1998.

[51] Int. Cl.$^7$ ........................................... A61F 5/00
[52] U.S. Cl. .................. 602/27; 602/5; 602/16; 602/23
[58] Field of Search .................... 602/5, 16, 20, 602/21, 26, 27, 28, 29; 623/18–21, 27, 30, 31, 40, 47, 48, 57, 59, 60

[56] References Cited

U.S. PATENT DOCUMENTS

| | | |
|---|---|---|
| 4,771,768 | 9/1988 | Crispin . |
| 4,962,760 | 10/1990 | Jones .......................................... 602/27 |
| 5,368,551 | 11/1994 | Zuckerman . |
| 5,429,588 | 7/1995 | Young et al. . |
| 5,672,152 | 9/1997 | Mason et al. . |
| 5,676,642 | 10/1997 | Peters . |
| 5,716,335 | 2/1998 | Iglesias et al. . |

*Primary Examiner*—Kim M. Lee
*Attorney, Agent, or Firm*—John F. Salazar; Thomas B. McGurk; Middleton & Reutlinger

[57] ABSTRACT

An ankle brace with a single piece hinge, interchangeable stirrup and pivot legs and an adjustable strap position fastener for protecting and exercising an injured ankle or for use with other orthopedic devices is described herein. The ankle brace pivots around a singular pivoting point on both the interior and the exterior portion of the lateral support members of the stirrup portion of the brace. The pivoting hinge of the ankle brace does not require use of metal rivets or bulky hinges and may be easily connected together by the wearer or manufacturer. The separable hinge design of the ankle brace described herein is sufficiently strong to provide substantial lateral support while allowing for forward and backward flexing of the ankle. The design also allows for interchanging the stirrup portion of the brace with different inner and outer pivot legs.

16 Claims, 7 Drawing Sheets

ANKLE BRACE WITH REMOVABLE SINGLE PIECE HINGE

This application claims benefit of provisional application 60/073,098, filed Jan. 30, 1998.

BACKGROUND OF THE INVENTION

1. Field of the Invention

The present invention relates to orthopedic devices and in particular ankle braces and more particularly to ankle braces which allow flexing of the ankle forward and backward, plantar-flexion and dorsiflexion, while preventing the ankle from flexing inward or outward, inversion or eversion, in order to promote healing of an injured ankle or prevent injury to an injury prone ankle during exercise. Particularly, the present invention relates to orthopedic devices and ankle braces which have a removable or detachable single piece hinge.

2. Discussion of the Prior Art

Ankle injuries are among the most common injuries in sports. In order to protect the ankle, many athletes have wrapped the ankle area with adhesive tape. The application of tape is expensive both because it is time consuming and because of the tape itself. It is also not very effective because the tape loosens quickly after exercise has begun. The use of exercise tape has also been shown to weaken ankles if used over a long period of time because it causes a loss of plantarflexion and dorsiflexion.

When an ankle is injured, the traditional method for promoting healing is to apply pressure to the area to reduce swelling and to prevent lateral movement of the ankle. The method of applying pressure to the ankle limits the range of motion over the ankle. When large areas are covered by a compression device, the material in contact with the foot must be fairly flexible or soft, such as an elastic bandage or an air bag, in order to avoid discomfort to the wearer and provide the amount of flexibility and movement required for athletic flexing of the ankle joint. This severely limits the amount of pressure that can be applied to the injury site in order to reduce the swelling caused by the ankle injury. An additional drawback found when air bag type devices are utilized is that the ankle and foot directly contact the bag in order to move, causing irritation of the skin. This irritation may be caused from the friction incurred by such contact which, in turn generates heat is which is not desirable to add to a swollen area of the body.

Another treatment method is to exercise the joint to promote healing. Exercise brings greater blood flow to the area and prevents the atrophy of the muscles involved. The current trend in medicine is to promote exercise as soon as possible. However, in traditional treatment methods, the ankle could not be properly exercised until after the compression device was removed thereby greatly delaying the exercise therapy. It is therefore desirable to provide an orthopedic device which allows exercise of the injury site while additionally resisting mobility in the direction which would irritate the injury.

As indicated, one method to promote healing of the ankle is preventing lateral movement of the ankle thereby allowing forward and backward flexing but preventing inward and outward flexing. The wearing of an ankle brace provides such protection while preventing inflammation of the injured ankle areas. Visually this forward and backward flexing is based upon a brace which is hinged in such a way to pivot backwards and forwards.

Most prior art devices that provide for pivoting of the ankle in addition to providing lateral support thereof are connected at the pivot point by an undetachable hinge or rivet. This type of non-detachable but pivotable connection between the stirrup and the pivot legs proves burdensome in both manufacturing and wearability issues. During manufacturing, when a rivet or other metal pivoting joint needs to be applied, a secondary assembly and additional attachment steps is required to inner-connect the separate portions of the ankle brace. Additionally, from the wearer's perspective, these types if pivoting joints add bulk and weight to the ankle brace.

SUMMARY OF THE INVENTION

The present invention provides an ankle brace which pivots along the same axis as the ankle and which has an easily separable, non-permanent single piece pivoting hinge.

The ankle brace of the present invention incorporates an ankle brace having a stirrup which is pivotally connected to an inner and outer pivot leg in combination with an adjustable strap positioning fastener for protecting and exercising an injured ankle. The hinge connection between the inner and outer legs of the stirrup and the inner and outer pivot legs is a single piece hinge minimizing the content of the overall brace and simplifying the overall construction of the ankle brace. The adjustable strap positioning means acts to firmly attach the pivoting legs of the ankle brace to the wearer. On the interior of the inner and outer pivot leg is attached softening pads which are secured to said pivot legs by VELCRO or other attachment means.

It is therefore an object of the present invention to overcome the deficiencies outlined above. It is a further object of the present invention to remove the assembly step traditionally required for pivoting ankle braces wherein a metal rivet or other permanent pivoting joint is required. It is a further object of the present invention to remove the hardware and extra weight present in prior art ankle braces.

More particularly, the present invention includes an ankle brace to be worn by a wearer to prevent ankle injury or encourage healing of an injured ankle, including a heel stirrup having a flat base portion and an inner and outer upright leg, inner and outer pivot legs which are pivotally attached to the inner and outer legs along inner and outer pivot points respectively.

Another object of the present invention is to provide axial movement of the ankle while additionally providing lateral support in order to prevent inversion or eversion of the ankle. It is a further object of the present invention to provide the greatest possible flexing of the ankle forward and backwards while keeping the pivot point of the ankle brace detachable yet providing significant lateral support and protection.

Another object of the present invention is to provide an ankle brace which allows flexing of the ankle forward and backwards, while also providing interchangeable parts for the stirrup portion of the brace and the individual pivot leg members.

The use of the ankle brace of the present invention provides the optimum combination of pressure applied to the injured area to reduce swelling and flexibility of the joint to permit exercise which promotes healing and reduces muscle atrophy. In this way a single brace provides the benefits both of a compression strategy and an exercise strategy to promote healing while protecting the ankle from further injury.

The present invention provides an ankle brace which meets all of the objectives outlined above. The present invention has a stirrup portion which is pivotally connected to inner and outer pivot legs, said pivot legs having on the interior thereof softening pads for compression directly against the wearer's leg or ankle. Additionally, a connecting strap is provided for tightening the inner and outer pivot legs in combination with the softening pads directly against the leg is while also providing a unique single piece pivoting or attachment hinge which allows for a maximum forward and backward flexing while also providing significant lateral support for the ankle. The single piece hinge of the present invention does not utilize rivets or other metallic hinge means which are commonly found in prior art braces. The hinge of the present invention utilizes a pivot button located on a flexing tab which is inserted into a thickened head portion of each upright leg of the stirrup. The stirrup and pivot legs of the ankle brace described herein are fully detachable from each other yet provide for a simple and rotatable attachment means which will not become easily detached through athletic activity.

DESCRIPTION OF THE PREFERRED EMBODIMENTS

Figure 1:
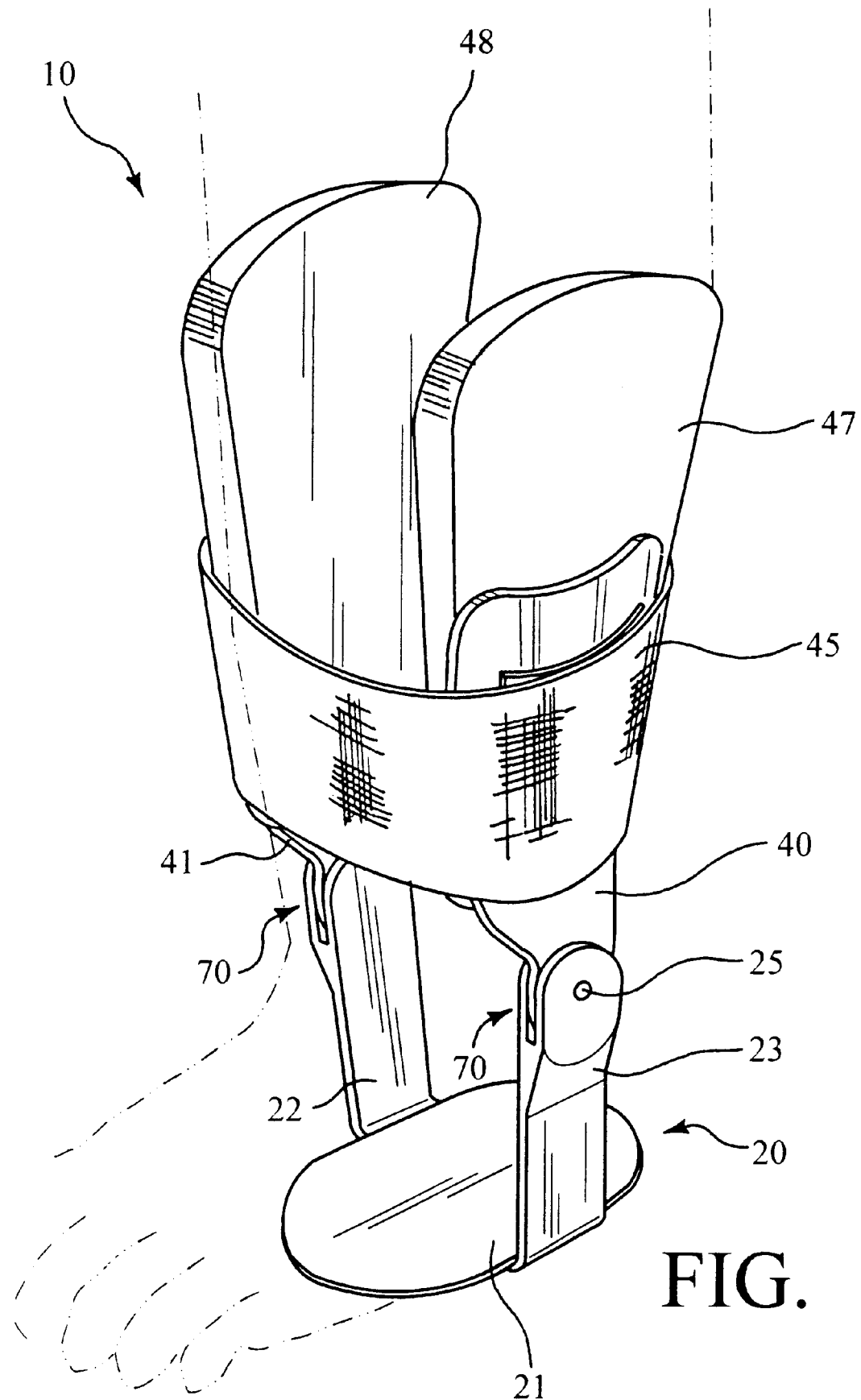
FIG. 1 is a perspective view taken from the front left side of an ankle brace made in accordance with the present invention.

The ankle brace 10 of the present invention is shown in FIG. 1. In this figure, the stirrup 20 of the ankle brace is shown as being comprised of a flat base portion 21, an inner upright leg 22 and an outer upright leg 23. Pivotally attached to the inner and outer upright legs 22 and 23 of stirrup 20 are outer pivot leg 40 and inner pivot leg 41. Such rotatable connection to the stirrup 20 allows the inner and outer pivot legs 40 and 41 to move forward and backwards rotating about pivot point 25 while additionally providing lateral support through upright legs 22 and 23. Attached to the interior of the inner and outer pivot legs 40 and 41 are inner and outer softening pads 47 and 48 which contact directly against the wearer's leg. Wrapped around the exterior of the inner and outer pivot legs 40 and 41 is the connecting strap 45 which enables the ankle brace 10 to be securely tightened around the wearer's leg. The inner and outer pivot legs 40 and 41 are easily detachable from stirrup 20 while at the same time they provide strong lateral support to the ankle through legs 22 and 23.

The stirrup 20 of the present invention is substantially a "U" shape and is comprised of the flat bottom portion 21 and the inner and outer upright legs 22 and 23. Both inner and outer upright legs 22 and 23 extend substantially vertically from the flat base portion 21. The stirrup 20 may be comprised of a strong thermoplastic material strong enough to prevent lateral shifting of the ankle retained between the inner and outer upright legs 22 and 23. The upright legs 22 and 23 may also be slightly offset to compensate for the typical slight outward pronation of the wearer's ankle.

Figure 3:
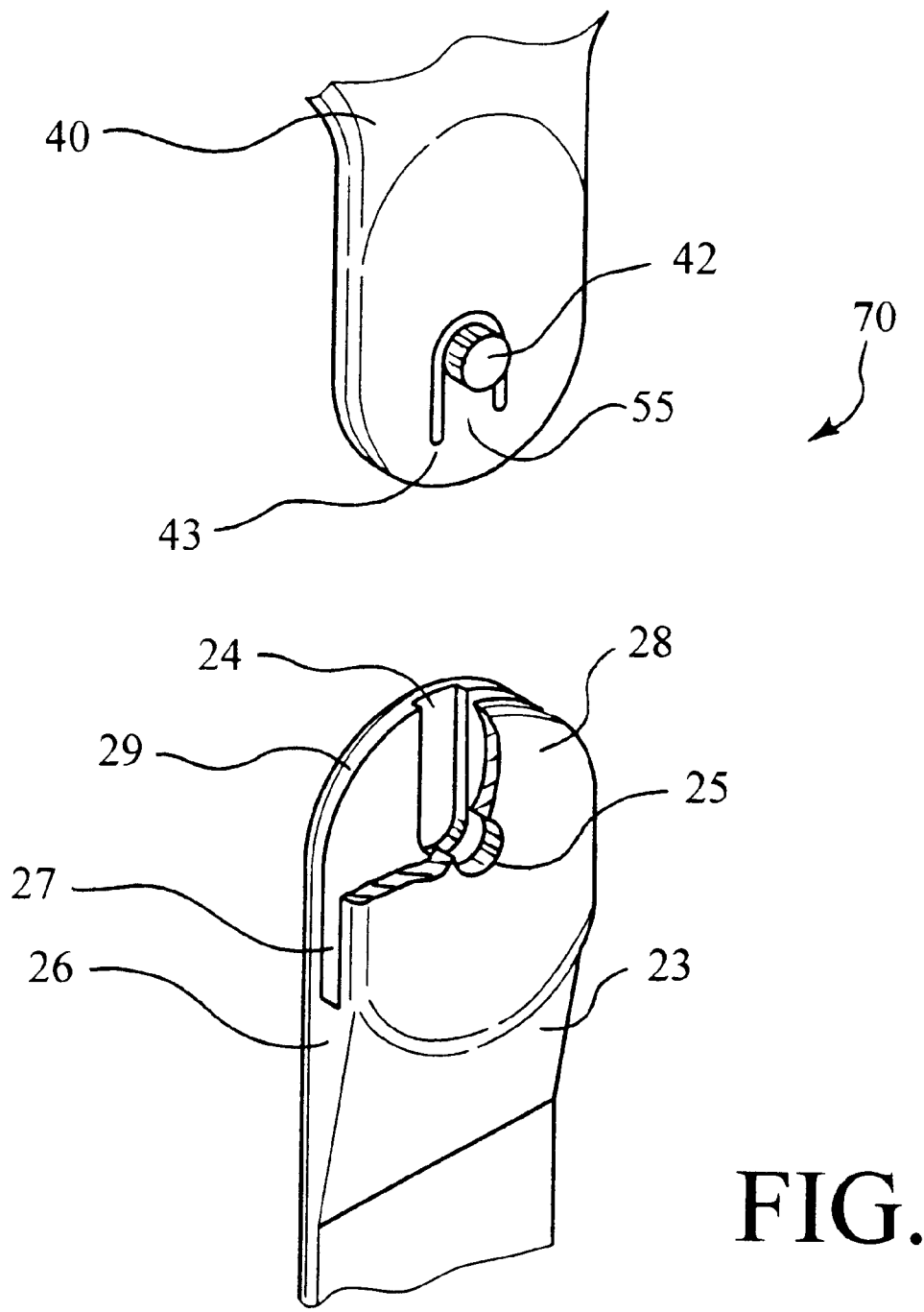
FIG. 3 is a close-up partial cutaway view of the removable hinge of the ankle brace shown in FIG. 1.

Shown more closely in FIG. 3 is the hinged or pivoting means 70 of the present invention wherein the thickened head portion 26 of outer upright leg 23 is shown in cross section. An ovalized channel 27 is centrally cut into the interior of the thickened ovalized head portion 26 of upright legs 22 and 23. The ovalized channel 27 formed in the head portion 26 creates inner and outer support post 29 and 28 respectfully. Channel 27 is of sufficient width to receive flange portion 43 is of the outer pivot leg 40. Ovalized flange 43 is formed on the bottom distal edge of each of said inner and outer pivot legs and each is inserted into channel 27 between inner and outer support posts 29 and 28 so that pivot button 42 fits within pivot point aperture 25 and rotates therein. Pivot button 42 of outer pivot leg 40 rests upon the outer periphery of flexing tab 55. Flexing tab 55 is formed from an inverted U-shaped cutaway section out of said ovalized head of flange 43. Deformable tongue or flexing tab 55 deflects backwards sufficiently so that pivot button 42 slides in between outer and inner support posts 28 and 29 causing flexing tab 55 to depress into elongated recess 24. Elongated U-shaped recess 24 is sufficiently deep enough such that tab 55 may be depressed sufficiently that pivot button 42 easily slides against outer support post 28 and reflexes into position after full insertion of the flange 43 into channel 27 such that pivot button 42 extends through pivot point aperture 25 of outer upright leg 23.

Figure 3A:
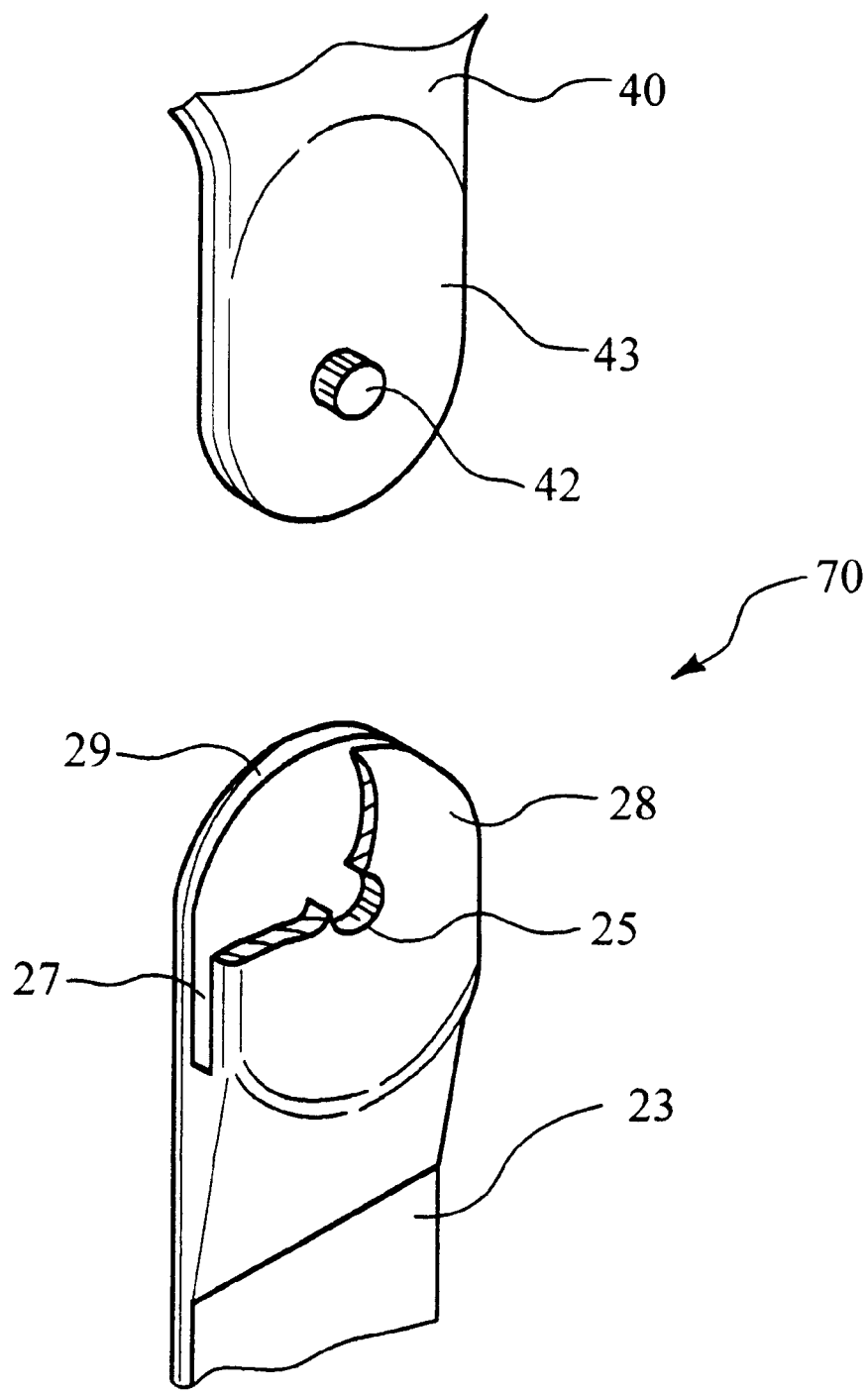
FIG. 3A is a close-up partial cutaway view of an alternative embodiment hinge of the present invention wherein the removable hinge of the ankle brace shown in FIG. 3 does not have a compression channel or a deformable tongue containing the pivot button.

Alternatively, as shown in FIG. 3A, a simpler embodiment is disclosed wherein the flexing tab 55 is removed from the overall design. In this embodiment, inner and outer support posts 28 and 29 which form the ovalized channel 27 receiving the flange portion 43 of the pivot leg 40 deform sufficiently enough that a flexing tab is not required for insertion of the pivot button 42 into aperture 25. As the material which the pivoting means 70 is comprised of consists of a resilient but slightly deformable thermoplastic material, assembly of the hinge is easily completed without the need for the flexing tab or compression channel. In all of the designs, significantly the pivoting means 70 is comprised of a single piece hinge made of unitary construction, single piece in that the comprised hinge does not require in the introduction of a secondary rivet or attachment means, as is required in the prior art. Thus, assembly of the ankle brace is marked by a reduction in manufacturing steps and parts. Further, the designed unitary or single piece hinge is sufficiently stable to provide for lateral support and movement of the ankle once the brace is in place around the users ankle.

As can be seen in FIG. 3, flange 43 of outer pivot leg 40 is rounded at the bottom most portion which matches the curvature of channel 27 formed in thickened head portion 26 of the outer upright leg 23. This matching curvature of the flange 43 and channel 27 allows the inner and outer pivot legs 40 and 41 to rotate along a wide range while also providing vertical support of the outer pivot leg by the outer upright leg 23. It is preferred that the rounded flange portion of the outer pivot leg not directly contact the bottom most portion of the channel 27. Additionally, the elongated recess 24 formed in the support post of the thickened head portion 26 is ramped so that the deepest portion of the recess is formed at the top of the inner support post 29 while, closer to the pivot point aperture 25, the recess has less depth. This ramp design of the elongated recess forces flexing tab 55 and pivot button 42 outward as the flange 43 is inserted farther into channel 27. However, the depth at the bottom most portion directly adjacent to the pivot point aperture 25 must be sufficiently deep enough to allow the pivot point button 42 to be pushed inwards so that the flange 43 may be removed from the channel 27.

A benefit of this pivot means 70 as noted is that it provides substantial lateral support of the ankle while also preventing the inadvertent removal of the flange 43 from the channel 27 during athletic activity. The design as shown in the figures does not require the additional assembly step noted in the prior art wherein metal rivets are utilized to connect the upright legs of the stirrup 20 with the outer and inner pivot legs 40 and 41. This manufacturing and assembly of the ankle brace 10, and particularly of the pivot means 70 of the present invention, is substantially easier. Further, the added bulk of having a metal joint is further moved. Finally, the interchangeability of the stirrup 20 and the pivot legs 40 and 41 adds to the ease of repair and replacement of portions of the brace 10. Thus, if a wearer requires varying size portions for the flat base portion 21 and pivot leg portions 40 and 41, an entire new brace assembly need not be built.

Figure 2:
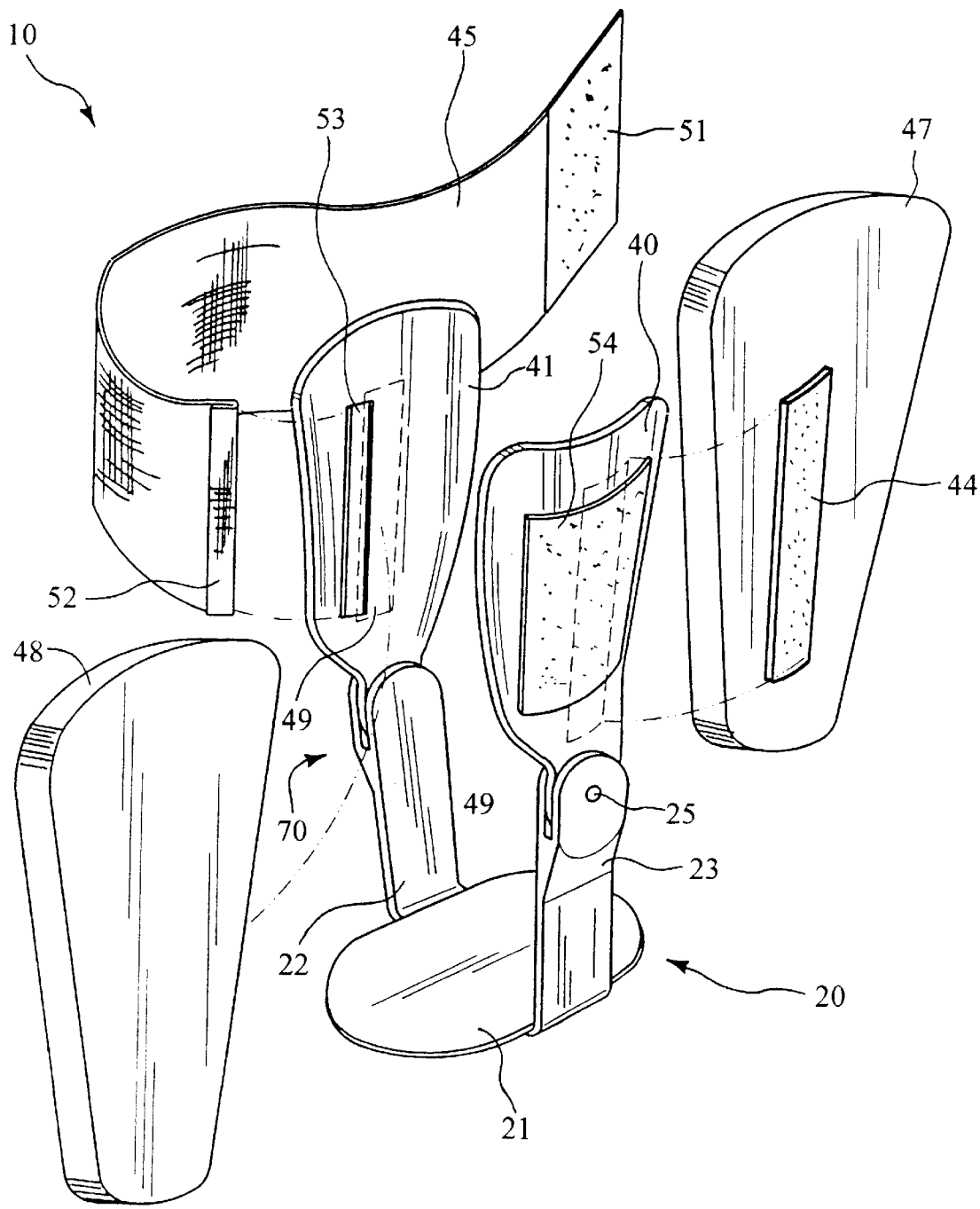
FIG. 2 is an exploded perspective view of the ankle brace of FIG. 1.

Turning to FIG. 2, an exploded view of the ankle brace 10 of the present invention is shown wherein the inner and outer softening pads 47 and 48 are detached from the outer and inner pivot legs 40 and 41. Softening pad 47 has attached thereon loop connector pad material 44 which is of a hook and loop type fastening means such as VELCRO and the like. Matching hook connector material 49 is placed on the interior side of the outer pivot leg 40 and is shown in phantom. Matching hook connector material 49 is placed on the interior portion of inner pivot leg 41. The hook connector material 49 placed on the interior of the pivot legs mates with loop connector pad material 44 which is located on the exterior surface of softening pad 47 and 48. Softening pad 47 and 48 as indicated, directly contact the wearer's leg and is made of a soft pliable material such as EVA or other similar type material.

Compressing the outer pivot leg 40 and inner pivot leg 41 as well as softening pads 47 and 48 against the legs is connecting strap 45 which is made of a nylon material and which circumscribes the wearer's leg and the pivot legs 41 and 40. Cuff loop 52 located at one end of the connecting strap 45 attaches into mating edge surface 53 of the inner pivot leg 41. Connecting strap 45 circumscribes the pivot legs and softening pads to compress them against the wearer's leg. Additional loop type material 54 may be placed on the exterior surface of outer pivot leg 40 so that connecting strap 45 can securely attach thereto. Securing strap 45 will additionally have loop connecting material formed on the interior surface thereof generally at the mid point for attaching to the loop type material 54 on pivot leg 40. Hook connector material 51 located at the opposite end of connecting strap 45 as compared to the cuff loop 52 fully wraps around the wearer's leg and reattaches to exposed loop material on the outer surface of the connecting strap, not shown, in order to provide a secure compression attachment around the leg.

As can be seen in FIG. 2, unitary hinge or pivot means 70 is comprised of pivot legs 40 and 41 and can swivel about the pivot axis point 25 while providing lateral support by the inner and outer upright legs 22 and 23. The ankle brace of the present invention restrains against inversion and eversion of the ankle while allowing plantarflexion and dorsiflexion.

Base portion 21, while shown in FIG. 2 as being substantially oval in shape, may in fact be contoured so that it matches the shape of the mid-section of the foot. The hinge means 70 provided for herein is also significant in that the position of the hinges is such that they are in line with the ankle bones (malleoli) of the wearer as the medial malleoli is superior to the lateral malleoli.

Figure 4:
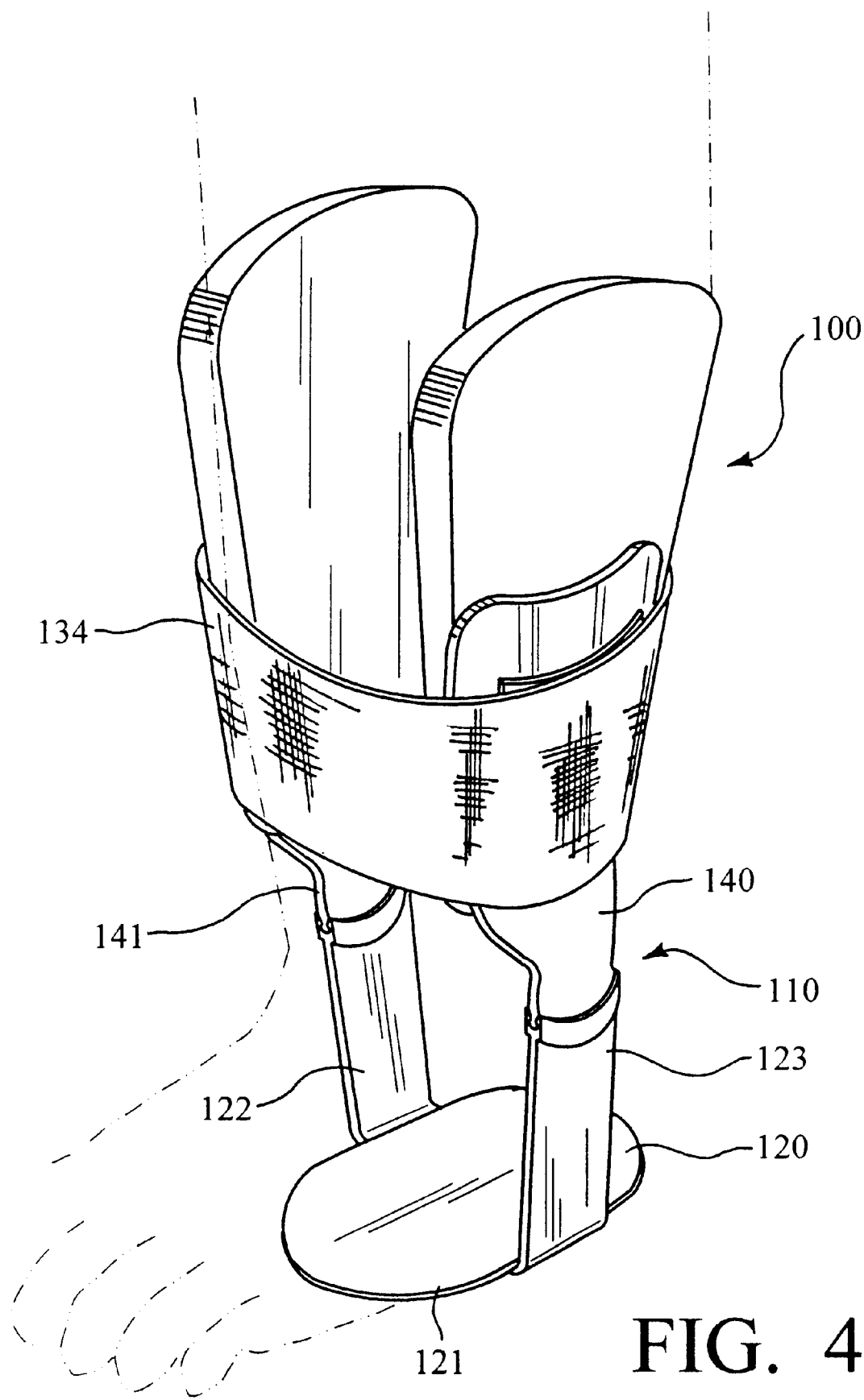
FIG. 4 is a perspective view taken from the front left side of an alternative embodiment of an ankle brace made in accordance with the present invention.
Figure 5:
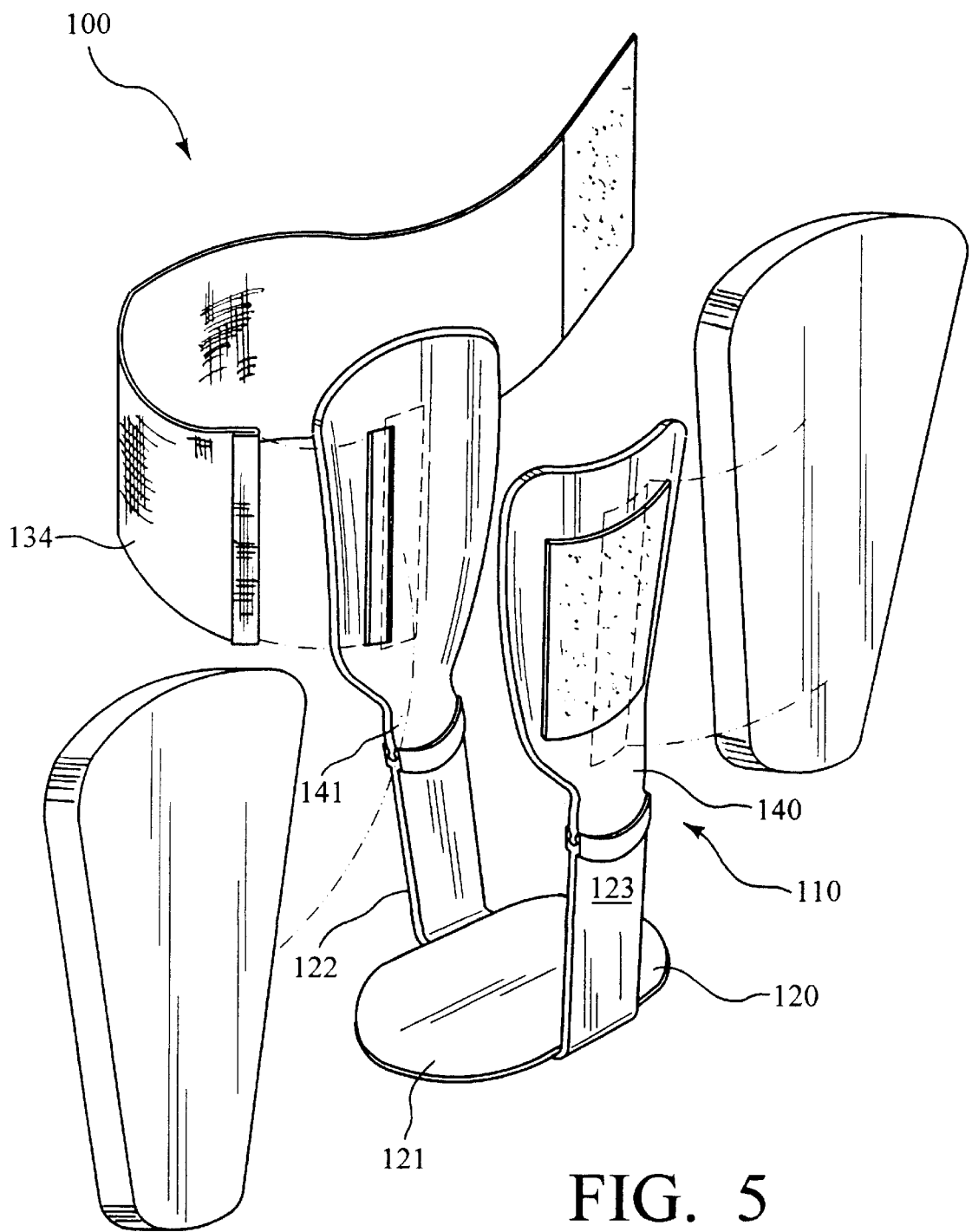
FIG. 5 is an exploded perspective view of an ankle brace of FIG. 4.
Figure 6:
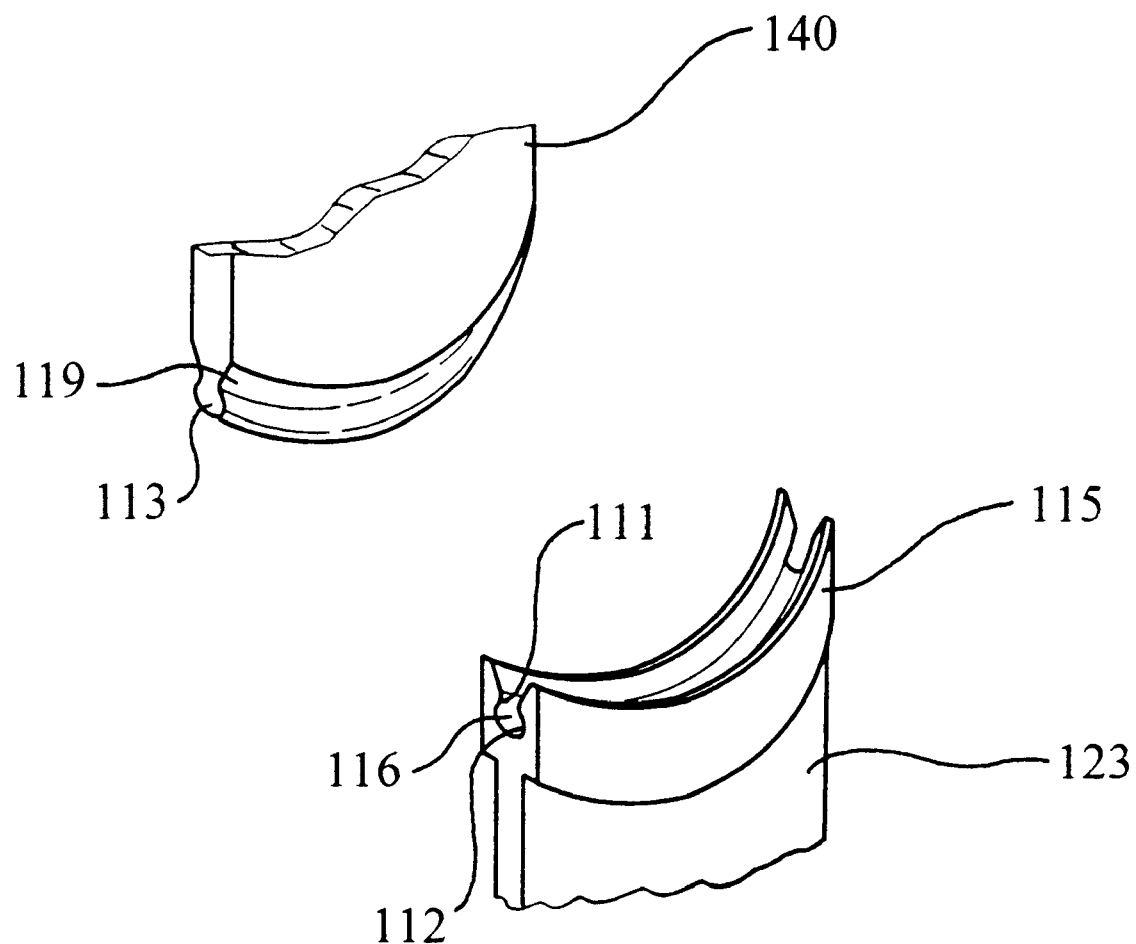
FIG. 6 is a close-up of the alternative embodiment hinge for the ankle brace shown in FIG. 4.

Shown in FIG. 4 is an alternative embodiment of the ankle brace 100. The hinge 110 of the ankle brace 100 as opposed to pivoting around a pivot button 42 swivels within a channel 116 shown in FIG. 7. Outer upright leg 123 has a thickened head portion 115 within which channel 116 is formed. As can be seen from the drawing, channel 116 has a narrowed ridge portion 111 and a widened area 112. The narrow ridge portion 111 retains the pivot leg 140 within channel 116. Pivot leg 140, as is shown in FIG. 7, has grooved flange 113 at its distal end. The groove 119 formed in flange 113 receives the narrow ridge portion 111 of channel 116. This channel and flange combination allows the pivot leg 140 to swivel within channel 116 forwards and backwards allowing axial flexing of the ankle. However, inner and outer upright legs 122 and 123 provide lateral support for the ankle preventing re-injury thereof. The flange and channel hinge design shown in FIG. 7 provides for smooth movement of the pivot leg 140 within channel 116. As is shown in FIG. 6, the overall design of the ankle brace 100 is similar to the previous design except for the hinge itself. Stirrup 120, base portion 121 and inner and outer upright legs 122 and 123 are made of a stiff or rigid material providing adequate lateral support of the ankle. Forward flexing of the leg and the ankle is provided for by the channel 116 and flange 113 hinge design. Attachment to the wearer's leg is similarly provided for by an attachment strap 134 which has standard hook and loop type attachments for securing the pivot legs 140 and 141 to the wearer's leg.

The foregoing detailed description is given primarily for clearness of understanding and no unnecessary limitations are to be understood therefrom for modifications will become obvious to those skilled in the art upon reading this disclosure and may be made without departing from the spirit of the invention or the scope of the appended claims.

What is claimed is:

1. An ankle brace having a unitary hinge, comprising:
    a stirrup having a flat bottom portion and an inner and outer upright leg, each of said inner and outer upright leg having an upper and lower end, said lower end attached to said flat bottom portion, said upper end having a an inner and outer support post forming an ovalized channel;
    inner and outer pivot legs pivotally attached to said inner and outer upright legs, each of said pivot legs having an ovalized flange portion at one distal end, said flange portion having a pivot button centrally aligned thereon and extending outwardly therefrom;
    wherein said outer support post for each of said inner and outer upright legs has an aperture formed therethrough receiving said pivot button of each of said inner and outer pivot legs.

2. The ankle brace of claim 1 wherein said ovalized flange portion of each of said inner and outer pivot legs has a flexing tab, said flexing tab having said pivot button contained thereon.

3. The ankle brace of claim 1 wherein said flexing tab has an inverted U shaped cutaway portion forming said flexing tab.

4. The ankle brace of claim I wherein said inner support post for each of said inner and outer upright legs has an elongated U-shaped slot formed therein.

5. The ankle brace of claim 1 wherein said ovalized channel is formed in a thickened portion of the upper end of said inner and outer upright leg.

6. An ankle brace having a single piece removable hinge, comprising:

a stirrup having a flat bottom portion and an inner and outer upright leg extending substantially vertically therefrom, said inner and outer upright leg affixed at their lower end to said flat bottom portion and having at the opposite end a thickened ovalized head portion;

inner and outer pivot legs pivotally attached to said ovalized head portion of said inner and outer upright legs and extending upwardly therefrom;

a first and a second softening pad removably attached respectively to the interior of said inner and outer pivot legs;

a removably attachable connecting strap circumscribing the exterior of said inner and outer pivot legs to compress them together.

7. The ankle brace of claim 6 wherein said ovalized head portion of said inner and outer upright legs has an ovalized channel formed therethrough and wherein said inner and outer pivot legs each have an ovalized flange portion at their bottom distal end.

8. The ankle brace of claim 7 wherein said ovalized flange portion of said pivot legs has a pivot button extending outward therefrom, said ovalized head portion of said inner and outer upright leg having a matching aperture for receiving said pivot button.

9. The ankle brace of claim 8 wherein said ovalized flange portion has an inverted U-shaped flexing tab having said pivot button formed centrally thereon and extending outward therefrom.

10. The ankle brace of claim 7 wherein said ovalized channel forms inner and outer support posts for each of said upright legs, said inner support post having an elongated U-shaped slot formed therein.

11. An ankle brace with interchangeable stirrup and pivot legs, comprising:

a stirrup having a flat bottom portion and an inner and outer upright leg extending upward therefrom, said inner and outer upright legs having an upper and a lower end and affixed at said lower end to said flat bottom portion;

inner and outer pivot legs removably attached to said upper end of each of said inner and outer upright legs of said stirrup;

pivot means allowing said inner and outer pivot legs to rotate freely within a channel formed on said upper end of said inner and outer upright legs.

12. The ankle brace of claim 1 further comprising:

a first and a second softening pad removably attached respectively to the interior of said inner and outer pivot legs;

a removably attachable connecting strap circumscribing the exterior of said inner and outer pivot legs to compress them together.

13. The ankle brace of claim 1 wherein said pivot means comprises:

a pivot button extending outward from an ovalized flange portion of each of said pivot legs;

an ovalized head portion formed on each of said inner and outer upright legs, said ovalized head portion having a first and a second support post and an ovalized channel formed therethrough, said ovalized flange portion rotating within said ovalized channel;

said pivot button extending through an aperture formed in said second support post of each of said inner and outer upright leg.

14. The ankle brace of claim 13 wherein said ovalized flange portion has an inverted U-shaped flexing tab having said pivot button formed centrally thereon and extending outward therefrom.

15. The ankle brace of claim 13 wherein said first support post has an elongated U-shaped slot formed on the interior wall thereof.

16. The ankle brace of claim 11 wherein said pivot means comprises:

said channel being an arcing channel formed on the upper end of said inner and outer upright legs, said arcing channel having a widened area and a narrow ridge portion;

said lower end of both of said pivot legs having a grooved flange for rotation within said arcing channel of both of said upright legs.

* * * * *

UNITED STATES PATENT AND TRADEMARK OFFICE
CERTIFICATE OF CORRECTION

PATENT NO.    : 6,146,350
DATED         : November 14, 2000
INVENTOR(S)   : Scott T. Morton It is certified that error appears in the above-identified patent and that said Letters Patent is hereby corrected as shown below:

Claim 3,
Line 62, change "claim 1" to -- claim 2 --;

Claims 12 & 13,
Change "claim 1" to -- claim 11 --;

Signed and Sealed this

Twentieth Day of November, 2001

Attest:

*Nicholas P. Godici*

NICHOLAS P. GODICI
*Attesting Officer*   *Acting Director of the United States Patent and Trademark Office*